US00PP23372P2

(12) United States Plant Patent
Ui et al.

(10) Patent No.: US PP23,372 P2
(45) Date of Patent: Jan. 29, 2013

(54) ***PETUNIA-CALIBRACHOA* PLANT NAMED 'SAKPXC009'**

(50) Latin Name: *Petunia-Calibrachoa* Hybrid (*P.×hybrida×C.×hybrida*)
Varietal Denomination: SAKPXC009

(75) Inventors: Akinobu Ui, Iwata (JP); Shin Ishikawa, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/200,676

(22) Filed: Sep. 28, 2011

(51) Int. Cl.
*A01H 5/00* (2006.01)

(52) U.S. Cl. ..... Plt./356.11

(58) Field of Classification Search ..... Plt./356.11
See application file for complete search history.

*Primary Examiner* — Annette Para
(74) *Attorney, Agent, or Firm* — Jondle & Associates, P.C.

(57) ABSTRACT

'SAKPXC009' is a new *Petunia-Calibrachoa* hybrid plant particularly distinguished by its pink flower color, excellent blooming ability and semi-creeping growth habit.

1 Drawing Sheet

Genus and species: *Petunia-Calibrachoa* Hybrid (*P.×hybrida×C.×hybrida*).

Variety denomination: 'SAKPXC009'.

BACKGROUND OF THE INVENTION

The present invention comprises of a new and distinct cultivar of *Petunia-Calibrachoa* (Petchoa) referred to by the variety name 'SAKPXC009'. Variety 'SAKPXC009' originated from an intergeneric hybridization in Kakegawa, Japan in October of 2004. The male parent was proprietary hybrid *Calibrachoa* line '2B-106A-1', which has a white flower color, large flower size and a creeping plant habit. The female parent was proprietary hybrid *Petunia* line '103K', which has a rose flower color, medium flower size and semi-mounding plant habit.

After crossing the parent lines, 1600 ovules were removed from flowers on the female parent and cultured by standard ovule culture techniques. In March 2005, intergeneric hybrid plantlets were transplanted to soilless media for greenhouse culture and acclimatization.

From July to November 2005, the plants were vegetatively propagated to produce rooted cuttings. Subsequently, the plants were transplanted to an open field and evaluated for flower color and plant growth habit. A plant was selected that had a pink flower color, an excellent blooming ability and semi-creeping plant growth habit. Plants of the selection were vegetatively propagated and then were evaluated in an open field. In June 2006, the breeder confirmed that the distinct characteristics of the selection were fixed and stable. The selection was named 'SAKPXC009'. All breeding work was conducted at Kakegawa Research station in Kakegawa Japan.

Plant Variety Protection for this variety was applied for in Japan on Oct. 8, 2010. 'SAKPXC009' has not been made publicly available more than one year prior to the filing of this application.

SUMMARY OF THE INVENTION

The following are the most outstanding and distinguishing characteristics of this new cultivar when grown under normal horticultural practices in Kakagawa, Japan.

1. Pink flower color;
2. Excellent blooming ability; and
3. Semi-creeping growth habit.

DESCRIPTION OF PHOTOGRAPHS

This new *Petunia-Calibrachoa* plant is illustrated by the accompanying photographs which show the plant's form, foliage and flowers. The colors shown are as true as can be reasonably obtained by conventional photographic procedures.

DESCRIPTION OF THE NEW CULTIVAR

Figure 1:
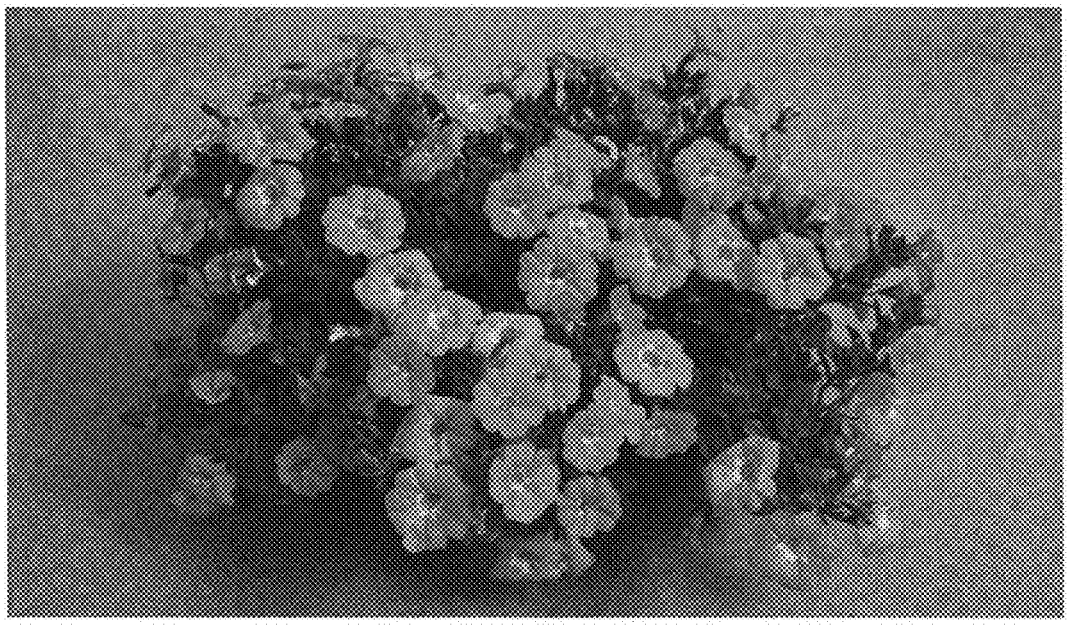
FIG. 1 shows overall plant habit.
Figure 2:
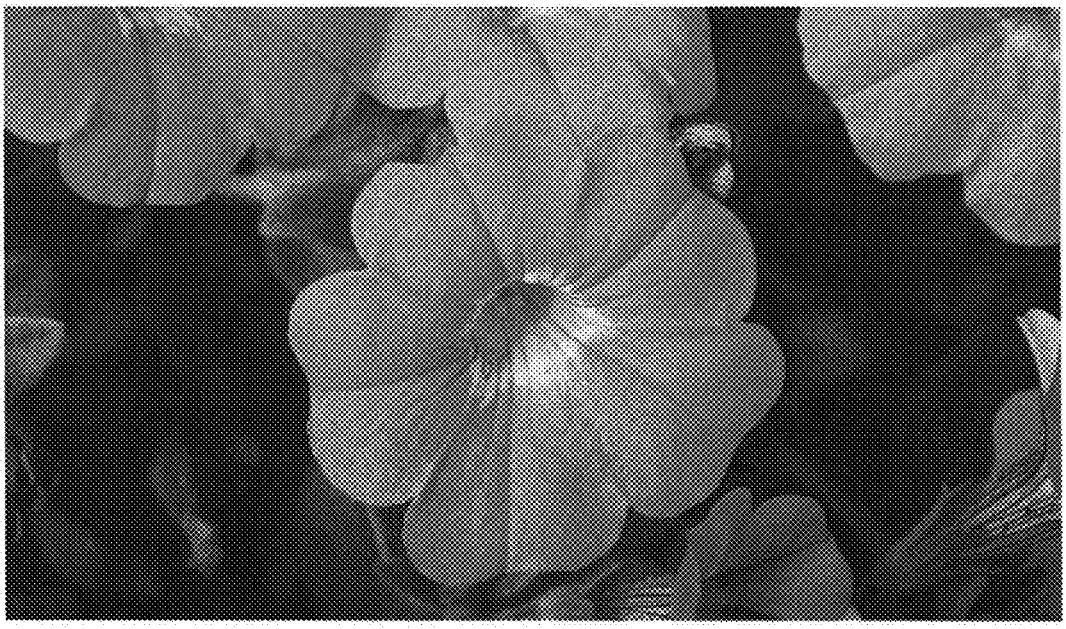
FIG. 2 shows the mature flowers.

The following detailed description sets forth the distinctive characteristics of 'SAKPXC009'. The data which define these characteristics were collected from asexual reproductions carried out in Salinas, Calif. The detailed description was taken from plants grown under greenhouse conditions for approximately 4 months from transplanting of rooted cuttings. Color references are to The R.H.S. Colour Chart of The Royal Horticultural Society of London (R.H.S.), $4^{th}$ Edition.

DETAILED BOTANICAL DESCRIPTION

Classification:

*Family.*—Solanaceae.

*Species.*—*Petunia-Calibrachoa* Hybrid (*P.×hybrida×C.×hybrida*).

*Common name.*—Petchoa, *Petunia-Calibrachoa.*

Parentage:

*Male.*—Hybrid proprietary *Calibrachoa* plant line '2B-106A-1'.

*Female.*—Hybrid proprietary *Petunia* plant line '103K'.

Plant description:

*Life cycle.*—Tender perennial.

*Form.*—Decumbent, branching.

*Habit.*—Spreading.

*Height.*—20.0 cm to 22.0 cm (from soil line to top of foliage).

*Spread.*—50.0 cm to 52.0 cm.

Propagation:

*Type cuttings.*—Vegetative cuttings.

*Time to produce a rooted cutting.*—4 weeks.

*Time to bloom from propagation.*—8 to 10 weeks.

Environmental conditions for plant growth: The terminal 1.0 to 1.5 inches of an actively growing stem was excised. The vegetative cuttings were propagated in four weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. For the first week, the cuttings were misted with water from overhead for 20 seconds, one time per hour. For the second week, the cuttings were misted one time every 2 hours for 10 seconds. After that time, the cuttings were misted occasionally until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:

*Stem color*.—RHS 144A (Yellow-green).
*Pubescence*.—Heavy.
*Pubescence color*.—RHS N155A (White).
*Stem description*.—Circular, cross-section.
*Stem diameter*.—2.0 mm to 3.0 mm.
*Stem length*.—1.0 cm. from soil line to first node; 17.0 cm to 18.0 cm total.
*Internode length*.—2.0 cm.

Leaves:

*Arrangement*.—Alternate.
*Shape*.—Elliptic.
*Apex*.—Obtuse.
*Base*.—Attenuate.
*Margin*.—Entire.
*Surface*.—Dull.
*Surface pubescence*.—Light.
*Pubescence color*.—RHS N155A (White).
*Venation*.—Pinnate.
*Length*.—4.0 cm.
*Width*.—2.0 cm.
*Color*.—Upper surface: RHS 137B (Green). Lower surface: RHS 137C (Green).
*Fragrance*.—Absent.

Flowers:

*Flowering habit*.—Indeterminate.
*Flower type*.—Solitary.
*Flowering requirements*.—Will flower so long as day length is greater than 12 hours and temperature exceeds 13° C.
*Duration of flowers*.—5 days.
*Flower depth*.—0.5 cm.
*Flower tube length*.—2.5 cm.
*Flower tube diameter*.—0.8 cm.
*Flower diameter*.—5.0 cm.
*Fragrance*.—Absent.
*Corolla*.—5 petals, fused. Type: The flowers are funnel shaped with five fissures and a shallow, yet slight, indentation of the petal tip at the midvein. Diameter: 5.0 cm. Tube color: Inner Eye zone has RHS 76D (Purple) at base of lobes/top of corolla tube. Corolla tube is RHS 13B (Yellow) with RHS 59A (Red-purple). Outer: RHS 10B (Yellow) with RHS 59A (Red-purple) veins.
*Flower buds*.—Surface: Pubescent. Length: 2.8 cm. Diameter: 1.0 cm. Shape: Ovate. Color: RHS 77A (Purple).
*Peduncle*.—Length: 2.5 cm. Diameter: 1.0 mm. Color: RHS 144B (Yellow-green). Texture: Dull, light pubescence. Pubescence color: RHS N155A (White).
*Pedicel color*.—RHS 144B (Yellow-green).
*Calyx*.—5 sepals fused below the middle.
*Sepals*.—Shape: Elliptical. Apex: Obtuse. Margin: Entire. Length: 1.7 cm. Width: 3.0 mm. Sepal color (both upper and lower surfaces): RHS 137A (Green).
*Petal*.—Shape: Spatulate. Lobe Length: 2.0 cm. Lobe Width: 2.5 cm. Apex: Truncate. Margin: Entire. Texture: Glabrous. Color: Upper surface: Closest to RHS N74A (Red-purple). Lower surface: Closest to RHS 76D (Purple) with sprays of RHS N74C (Red-purple) and RHS 59A (Red-purple) veins.

Reproductive organs:

*Stamens*.—Free.
*Stamen number*.—5.
*Anther color*.—RHS 1D (Green-yellow).
*Filament color*.—RHS 2C (Yellow).
*Pollen color*.—RHS 10B (Yellow).
*Ovary*.—Superior.
*Placenta arrangement*.—Central.
*Pistil number*.—1 (per inflorescence).
*Pistil length*.—1.5 cm.
*Stigma color*.—RHS 144A (Yellow-green).
*Style length*.—1.3 cm.
*Style color*.—RHS 144A (Yellow-green).

Fruit/seed set: No fruit or seeds produced.

Disease and insect resistance: 'SAKPXC009' has excellent resistance to rain, heat and drought. Temperatures below 10° C. are not optimal. Plants are susceptible to Botrytis, powdery mildew, various stem and root rots, and certain viruses, like Tobacco Mosaic Virus and Impatiens Necrotic Spotted Virus. Plants can be infested with aphids, leafminer, whitefly and various Lepitopdera.

COMPARISON WITH PARENTAL LINES AND KNOWN CULTIVARS

'SAKPXC009' is a new and unique variety of intergeneric *Calibrachoa-Petunia* owing to its pink flower color, excellent blooming ability and semi-creeping plant growth habit. 'SAKOST8202' is distinguished from its parents as described in Table 1.

TABLE 1

| Characteristic | 'SAKPXC009' | Female Parent: '103K' | Male Parent: '2B-106A-1' |
|---|---|---|---|
| Flower color | Pink | White | Rose |
| Plant growth habit | Semi-creeping | Creeping | Semi-mounding |

'SAKPXC009' is most similar to the commercial *Calibrachoa-Petunia* variety 'Kakegawa S89' (U.S. Plant Pat. No. 19,130), commercially known as 'SuperCal® Neon Rose'; however there are differences in the flower color as described in the Table 2 below (color references are to The Royal Horticultural Society Colour Chart, 4$^{th}$ edition):

TABLE 2

| Characteristic | 'SAKPXC009' | 'Kakegawa S89' (U.S. Plant Pat. No. 19,130) |
|---|---|---|
| Petal color, upper surface | RHS N74A (Red-purple) | RHS N66A (Red-purple) with 64A (Red-purple) veins |
| Petal color, lower surface | RHS 76D (Purple) and sprays of RHS N74C (Red-purple) with RHS 59A (Red-purple) veins | RHS N66C (Red-purple) with 142A (Green) veins |

We claim:

1. A new and distinct cultivar of *Petunia-Calibrachoa* hybrid plant as shown and described herein.

* * * * *